United States Patent [19]

Swedberg

[11] Patent Number: 5,314,593
[45] Date of Patent: May 24, 1994

[54] CAPILLARY TUBE WITH REVERSIBLE PROTEIN INTERACTION AND METHOD

[75] Inventor: Sally A. Swedberg, Waldbronn, Fed. Rep. of Germany

[73] Assignee: Hewlett-Packard Company, Palo Alto, Calif.

[21] Appl. No.: 32,913

[22] Filed: Mar. 18, 1993

[51] Int. Cl.$^5$ .................. G01N 27/26; G01N 27/447
[52] U.S. Cl. ................... 204/180.1; 204/299 R
[58] Field of Search ............ 204/299 R, 180.1, 182.8, 204/183.3

[56] References Cited

U.S. PATENT DOCUMENTS

| | | | |
|---|---|---|---|
| 4,680,201 | 7/1987 | Hjerten | 204/182.9 X |
| 4,931,328 | 6/1990 | Swedberg | 204/180.1 X |
| 5,006,313 | 4/1991 | Swedberg | 204/299 R X |
| 5,089,103 | 2/1992 | Swedberg | 204/299 R X |
| 5,089,106 | 2/1992 | Karger et al. | 204/180.1 X |

OTHER PUBLICATIONS

Maa et al., "Impact of Wall Modifications on Protein Elution in High Performance Capillary Zone Electrophoresis," *J. High Resol. Chromat.*, 14 (1991), pp. 65–67.
FMC Corporation publication "Introduction to Agarose," 1988, pp. 53–106.
Swedberg, "Characterization of Protein Behavior in High-Performance Capillary Electrophoresis Using a Novel Capillary System," *Analytical Biochemistry*, 185 (1990) pp. 51–56.
McManigill et al., "Factors Affecting Plate Height in High Performance Zonal Capillary Electrophoreses (HPZCE)," chapter 45 in Techniques in Protein Chemistry, Hugli, ed., San Diego: Academic Press (1989), pp. 468–478.
Lal et al., "The Use of Capillary Electrophoresis to Identify Cationic Proteins in Human Parotid Saliva," *Archs. Oral Biol.*, 37:1 (1992), pp. 7–13.
Holzman et al., "Preliminary Characterization of a Cloned Neutral Isoelectric Form of the Human Peptidyl Prolyl Isomerase Cyclophilin," *J. Biol. Chem.*, 266:4 (1991), pp. 2474–2479.
Tran et al., "Separation of Carbohydrate-Mediated Microheterogeneity of Recombinant Human Erythropoietin by Free Solution Capillary Electrophoresis," *J. Chromatography*, 542 (1991), pp. 459–471.
Lauer et al., "Capillary Zone Electrophoresis of Proteins in Untreated Fused Silica Tubing," *Anal. Chem.*, 58 (1986), pp. 166–170.

*Primary Examiner*—John Niebling
*Assistant Examiner*—John S. Starsiak, Jr.

[57] ABSTRACT

A method for treating capillary walls exposable to protein solutes is provided that promotes reversible interactions between the protein solutes and the wall. Thus a small bore capillary tube, useful for reproducible protein electrophoretic separations, includes an interfacial phase comprising agarose that is bonded to the bore. Pretreatment of the capillary walls with silylation reagents forms an intermediate layer that provides a determinable cathodic electroosmotic flow magnitude that remains constant even if the buffer pH fluctuates between 4–7. The modified capillaries can be used repeatedly and they exhibit selectivity in protein separations.

11 Claims, 5 Drawing Sheets

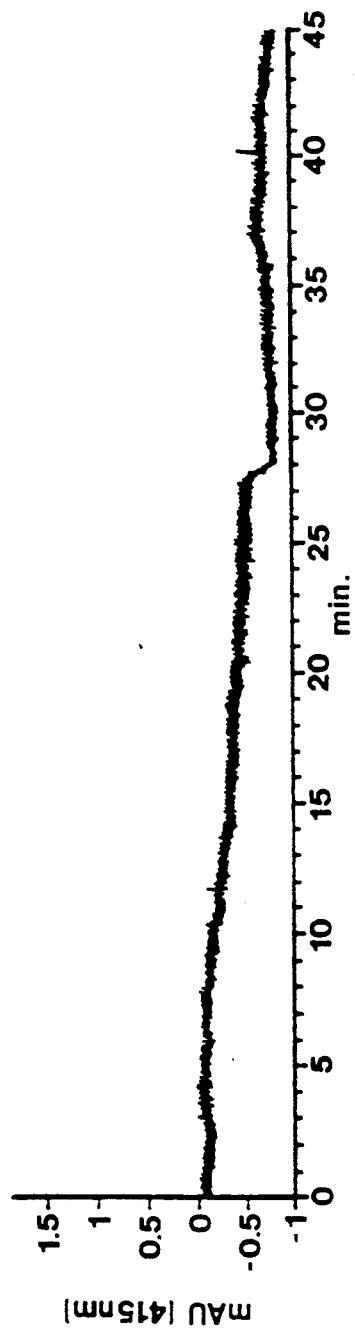
FIG._1a.
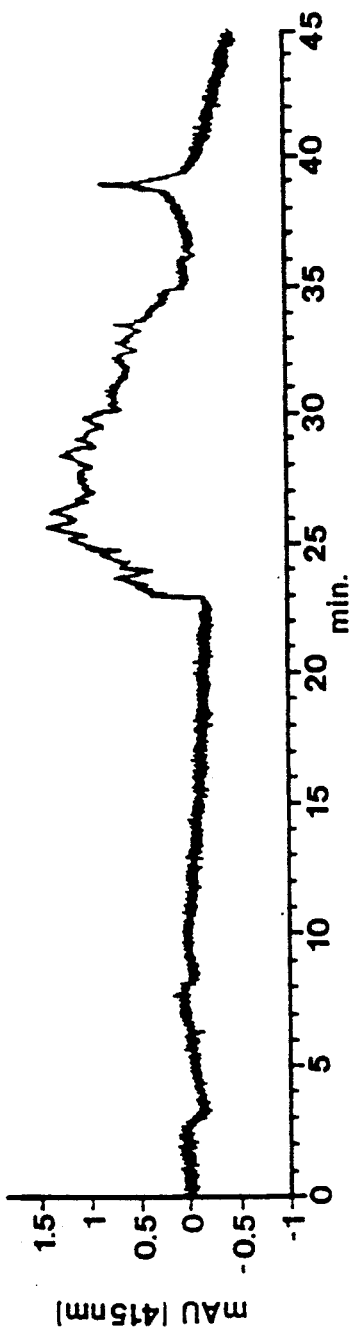
FIG._1b.
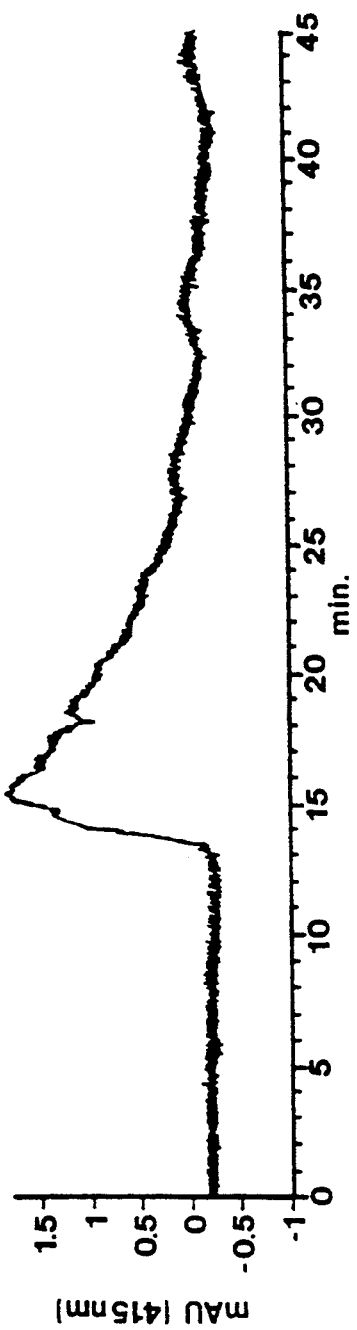
FIG._1c.

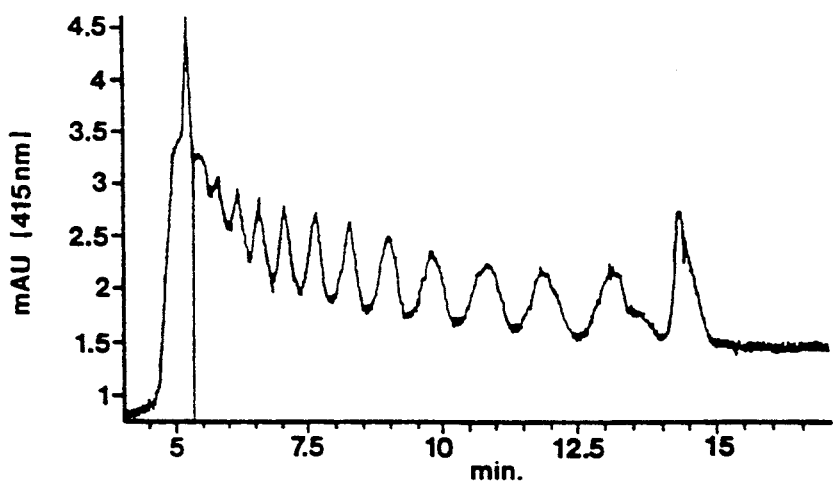
FIG._2a.
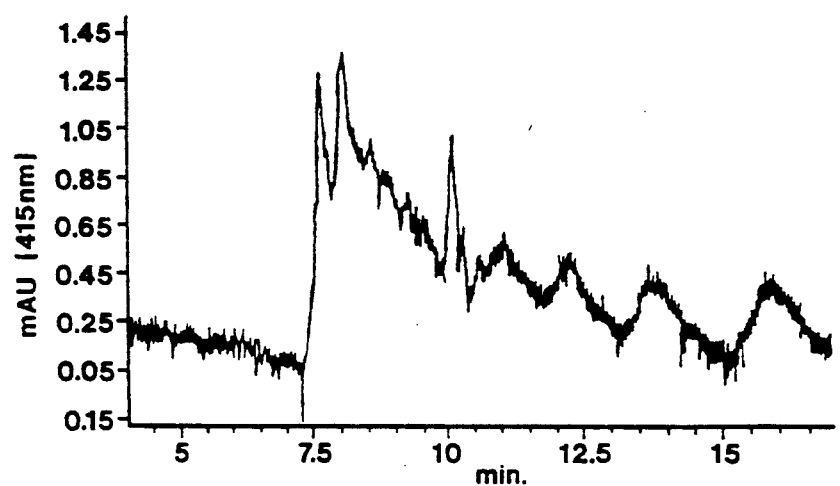
FIG._2b.
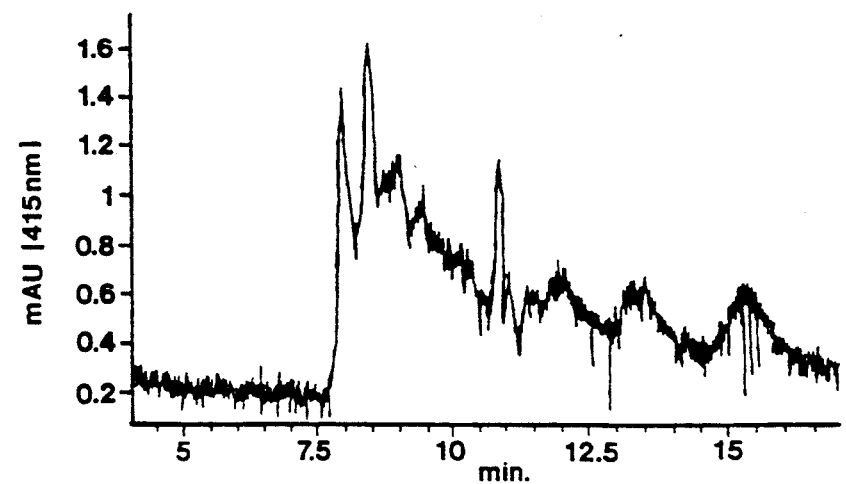
FIG._2c.

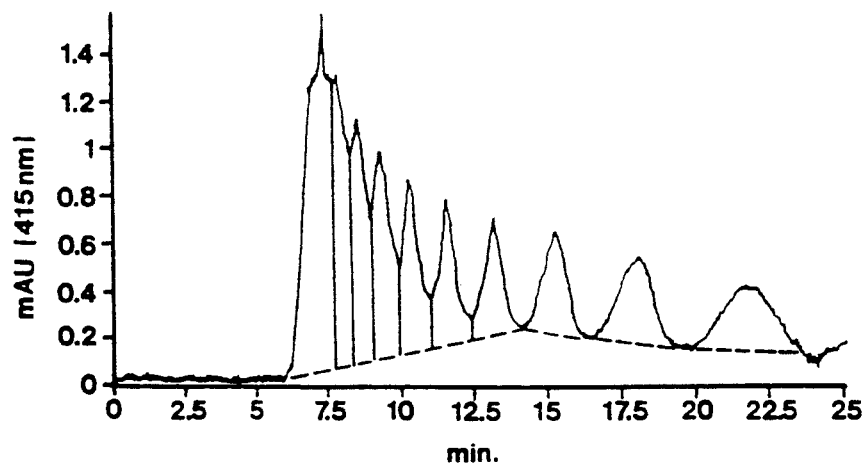
FIG._3a.
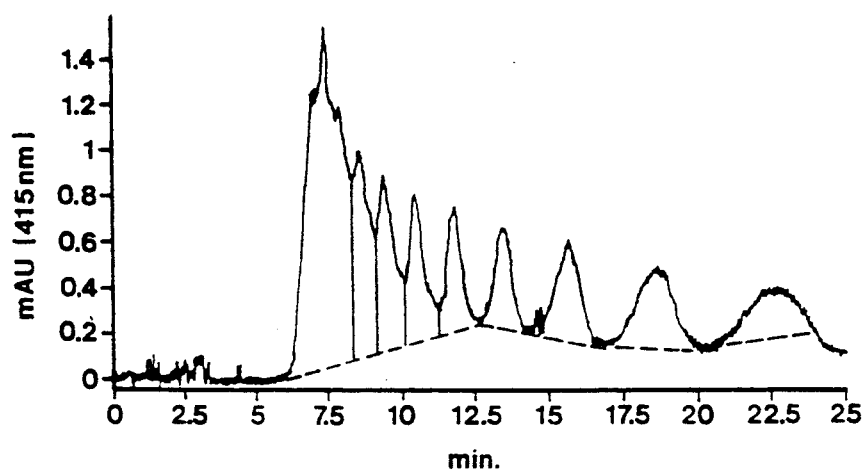
FIG._3b.
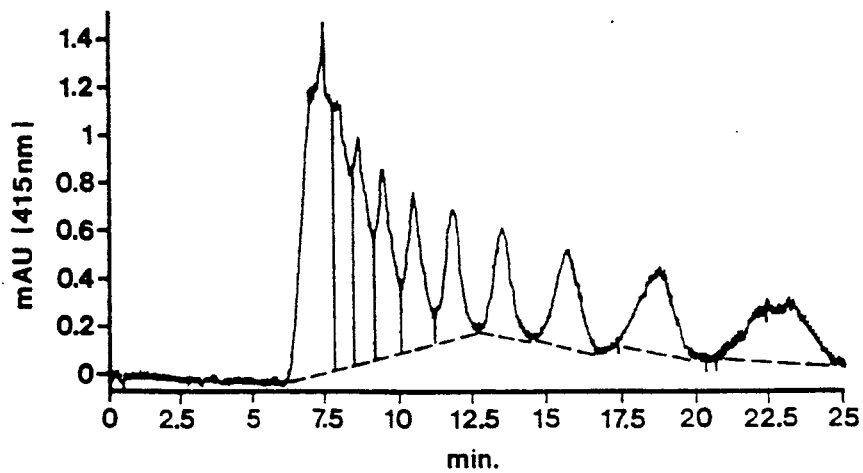
FIG._3c.

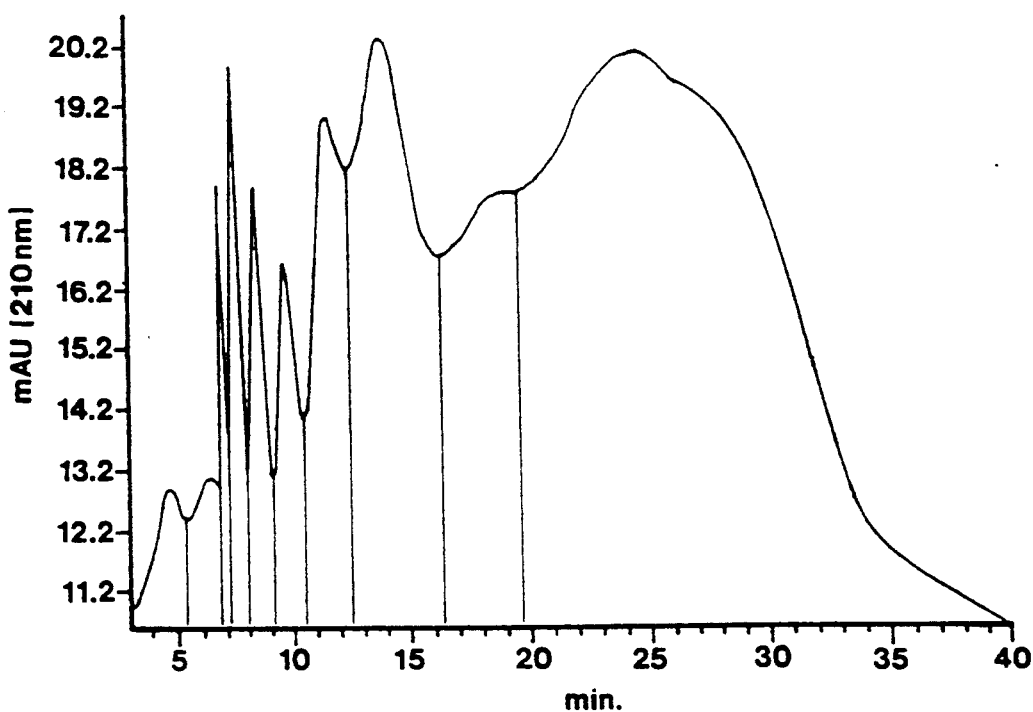
FIG._4a.
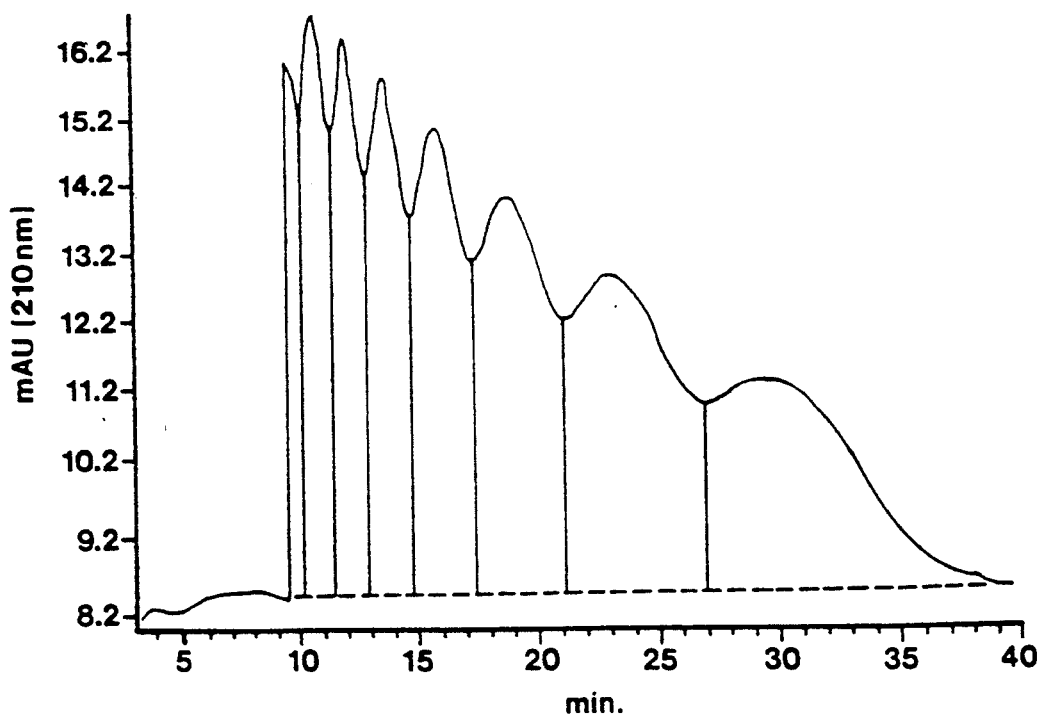
FIG._4b.

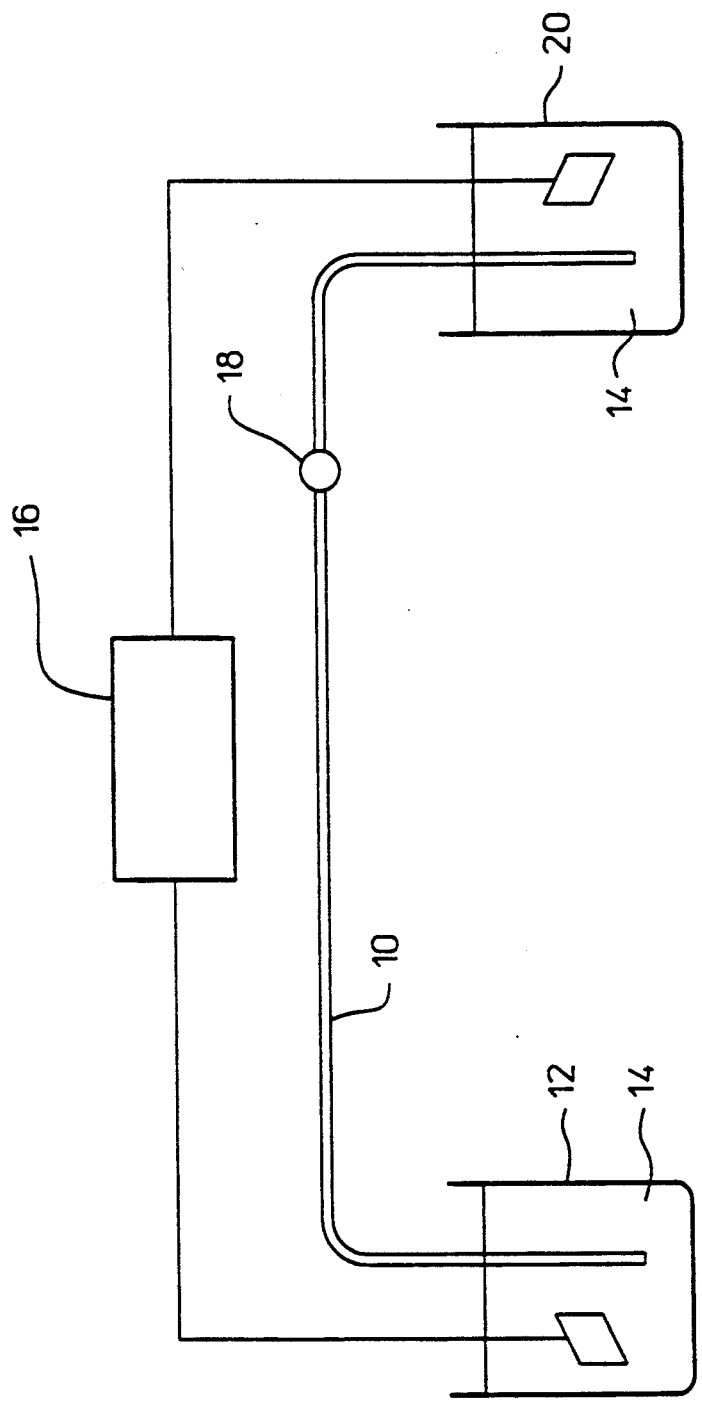
FIG._5

CAPILLARY TUBE WITH REVERSIBLE PROTEIN INTERACTION AND METHOD

FIELD OF THE INVENTION

The present invention generally relates to solid surfaces exposable to protein solutes, and particularly to capillaries used in electrophoretic separations by capillary zone electrophoresis.

BACKGROUND OF THE INVENTION

Capillary zone electrophoresis ("CZE") in small capillaries (less than or equal to 75 $\mu$) was first demonstrated by Jorgenson and Lukacs, and has proven useful as an efficient method for the separation of small solutes. *J. Chromatog.*, 218 (1981), page 209; *Anal. Chem.*, 53 (1981), page 1298. The mass transport of charged species past a single point of detection relies upon an electroosmosis effect generally described as the flow of a liquid in contact with a solid surface under the influence of a tangentially applied electric field. Attractive factors for electrophoretic separations by capillary zone electrophoresis are the small sample sizes, little or no sample pretreatment, and the potential for quantification and recovery of biologically active samples. For example, U.S. Pat. No. 4,675,300, inventors Zare et al., issued Jun. 23, 1987, describes theories and equipment for electrokinetic separation processes employing a laser-excited fluorescence detector. The system described by Zare et al. includes fused silica capillary with a 75 $\mu$ inside diameter.

High performance capillary electrophoresis ("HPCE") afforded the potential of extraordinary high efficiency separations of macromolecules. Unfortunately, the high efficiency first anticipated was based on the assumption that there would be no macromolecular/column interaction term in the unpacked (open tubular) column technique. It has been suggested by theoretical studies, which have been supported by experimental evaluation, Swedberg et al., (1989) in *Techniques in Protein Chemistry* (Hugli, ed.) Academic Press, San Diego, that this interaction (k') can be very small, and have a significant impact on the expected efficiency of macromolecular separations by HPCE.

Though the expectation of 1 to 2 million theoretical plates is unrealistic for HPCE, this does not diminish the impact HPCE may have on the automated separation of macromolecules. Recent publications from biosciences users highlight the advantages of HPCE for solving a specific separation problem which other traditional techniques were not able to solve. Holzman et al., *J. Biol. Chem.*, 266 (1991), pp. 2474–2479; Tran et al., *J. Chem.*, 524 (1991), pp. 459–471; and Lal et al., *Arch. Oral. Biol.*, (1992), pp. 7–13. The major obstacle on the effectiveness of the technique is the reproducibility of the column technology.

Jorgenson et al. had noted that separation of model proteins, such as cytochrome, lysozyme, and ribonuclease A, in untreated fused silica capillaries with a phosphate buffer at pH 7 was accompanied by strong tailing, and suggested this might be caused by Coulombic interaction of the positively charged proteins and the negatively charged capillary wall. Jorgenson et al., *Science*, 222 (1983), page 266.

Lauer et al., *Anal. Chem.*, 58 (1986), page 166, has reported that the Coulombic repulsion between some idealized proteins and the capillary wall of silica capillaries can overcome adsorption tendencies of these proteins with the capillary wall. They demonstrated separations of model proteins (ranging in molecular weight from 13,000 to 77,000) by varying the solution pH relative to the isoelectric point (pI) of the proteins to change their net charge. However, disadvantages of this approach are that (1) silica begins to dissolve above pH 7, which shortens column life and degrades performance, (2) only proteins with pI's less than the buffer pH can be analyzed, which drastically reduces the range of useful analysis, and (3) interactions which are not Coulombic may still occur even with proteins bearing a net negative charge due to the complexity of protein composition and structure.

Another approach to the problem of biopolymer or protein interactions has been to increase ionic strength. It has been demonstrated that this concept works in principle, but heating is also increased as ionic strength is increased. This heating tends to degrade the efficiency of separation. Increasing salt also decreases the mobility differences among proteins of similar charge and size thus further reducing separation efficiency.

Yet another approach to the problem of undesirable protein interactions with the capillary wall has been to coat the electrophoresis tube with a monomolecular layer of non-crosslinked polymer. Thus, U.S. Pat. No. 4,680,201, inventor Hjerten, issued Jul. 14, 1987, describes a method for preparing a thin-wall, narrow-bore capillary tube for electrophoretic separations by use of a bifunctional compound in which one group reacts specifically with the glass wall and the other with a monomer taking part in a polymerization process. This procedure results in a polymer coating, such as polyacrylamide coating, and is suggested for use in coating other polymers, such as poly(vinyl alcohol) and poly(vinylpyrrolidone). However, this method of capillary tube treatment tends to destroy the electroosmotic flow, and efficiencies are still rather low. These rather low efficiencies suggest that undesirable protein-wall interactions are still occurring.

More recently, in U.S. Pat. No. 4,931,328, issued Jun. 5, 1990, inventor Swedberg disclosed a method for preparing capillary tubes capable of exhibiting reduced protein interactions and controllable electroosmotic flow during electrophoresis. The capillary tube includes an interfacial layer that is covalently bonded to the inner wall of the capillary tube. The interfacial layer has a hydratable amphoteric phase that has a determinable isoelectric point and permits electroosmotic flow control by selection of solution pH. Employing this technique, Maa et al. demonstrated changes in protein selectivity on two deactivated capillaries due to the minimal protein-wall interactions. *J. High Resol. Chromatog.*, 14 (1991), pp. 65–67.

Another recent method of reducing interactions of protein solutes with capillary bore surfaces was disclosed in U.S. Pat. No. 5,006,313, inventor Swedberg, issued Apr. 9, 1991, in which the bore wall of a capillary tube is coated with a reduced interaction phase that includes a plurality of halogen atoms.

SUMMARY OF THE INVENTION

It is the object of the present invention to provide small bore capillary tubes that are useful for electrophoretic separations of solutes including macromolecules wherein interactions between the solutes and the bore are reversible.

It is another object to provide a method of modifying the inner wall of a capillary to design CZE phases with constant and predetermined electroosmotic flow (EOF) under varying pH conditions.

Yet another object is to provide a method for modifying the inner wall of a capillary with agarose which prolongs column life and enhances column performance in CZE.

Additional objects and advantages of the invention will become apparent to those skilled in the art upon examination of the specification and appended claims, as well as in practice of the present invention.

In one aspect of the present invention, a small bore capillary tube, useful for electrophoretic separations of protein solutes, comprises an interfacial phase that is covalently bonded to the bore. Protein solutes do not readily adhere to the modified surface during CZE; moreover, protein solutes that do adhere can be removed with mild buffer wash so that the capillary can be used repeatedly without significant reduction of separation efficiency or alteration of the electroosmotic flow.

In another aspect of the invention, a method for treating a surface exposable to protein solutes comprises modifying the surface by bonding at least one molecular layer of agarose to the surface. For silica-based surfaces, silylation of the surface prior to applying the agarose is preferred, although other interfacial layers may also be used between the agarose layer and the inner silica surface of the capillary. Moreover, by controlling the silylation conditions, it is possible to regulate the level of EOF.

Furthermore, using a layer including agarose within the capillary affords a method of fabricating capillaries that have a unique selectivity compared with existing electrophoresis capillaries, which use different chemical compositions in the interfacial layer. Because of this, the invention is able to resolve proteins that conventional systems are unable to separate adequately.

An embodiment of the invention suitable for electrophoretic separations of protein solutes comprises a capillary tube having an interfacial layer bonded to the capillary inner wall surface. The interfacial layer includes agarose that is covalently bonded to the surface. Capillary tubes as described by the present invention have been prepared and used in separations for various protein mixtures with good reproducibility and consistent performance upon repeated use.

BRIEF DESCRIPTION OF THE DRAWINGS

FIGS. 1(a), 1(b), and 1(c) are electropherograms of the same protein mixture after each of three successive injections into an untreated silicon capillary.

FIGS. 2(a), 2(b), and 2(c) are electropherograms of the same protein mixture after each of three successive injections into a silica capillary that was silylated with GOPS.

FIGS. 3(a), 3(b), and 3(c) are electropherograms of the same protein mixture after each of three successive injections into an inventive agarose modified capillary.

FIGS. 4(a) and 4(b) are electropherograms of the same protein mixture on a capillary modified with bovine serum albumin and a capillary modified with agarose, respectively.

FIG. 5 illustrates the main components of a CZE apparatus.

DETAILED DESCRIPTION OF THE PREFERRED EMBODIMENTS

The present invention provides a solid surface that is modified so as to have reversible interactions with protein solutes. "Reversible interactions" mean that when protein molecules adhere to the modified surface, they are readily removed under mild wash conditions. Mild conditions are those which do not adversely affect the structural integrity of the solid surface, but yet are effective to remove the proteins within a reasonable period of time. Specifically, when protein solutes adhere to a modified capillary wall during CZE before passing a point of detection, these proteins can be removed after CZE by washing with buffer or other mild solvent so that the capillaries can be used repeatedly without significant reduction in separation efficiency or alteration of the electroosmotic flow.

One particularly preferred application is for small bore capillary tubes, such as the tubes used in CZE. These tubes are usually up to 500 $\mu$, more typically about 20 $\mu$ to about 200 $\mu$, in internal diameter. For convenience, reference will hereinafter be to a small bore (less than about 500 microns) capillary tube with the bore having been modified in accordance with the invention. The modification is whereby a phase, capable of reversible interactions with protein solutes, is covalently bonded to the inside wall, as an interfacial layer between the inside wall of the capillary and the protein solutions present when in use.

The present invention is particularly relevant for CZE because in prior art HPCE the single greatest factor adversely affecting reproducibility in protein separations has been the irreversible interaction of the proteins with the capillary inner surface. It is known that when protein molecules irreversibly interact with the column surface the interaction changes the zeta potential in the interfacial layer. This in turn alters the EOF, for capillaries with EOF, and/or changes the surface selectivity. In either event, reproducibility is adversely affected.

The present invention is based in part on the discovery that agarose covalently bonded to capillary surfaces forms a stable interfacial layer that provides reversible protein-surface interactions. The inventive surface modification also prolongs column life and enhances column performance. In preparing inventive capillaries with a reversible interaction phase that is covalently bonded to the inner wall of silica based capillaries, silica based columns are preferably preconditioned and silylated as generally described in U.S. Pat. No. 4,931,328, inventor Swedberg, issued Jun. 5, 1990, and U.S. Pat. No. 5,006,313, inventor Swedberg, issued Apr. 9, 1991, both of which are incorporated herein. The silylation conditions can be chosen to deposit a few multilayers to bulk coatings on the capillary wall. Moreover, the amount of EOF can be reduced or eliminated by controlling the amount of silylation.

When the surface to be modified is silica based, it is preferably first hydrated and then treated with an organo- or chloro-silane having two functional end groups. The one functional group reacts specifically with the glass wall. Thus, one or two alkoxy groups (such as methoxy, acetoxy, methoxyethoxy or chloro) react with the silanol groups in the wall to form a stable, covalently bonded linkage. Concentrations of silylating reagent in aqueous solution from about 0.1 wt. % to about 1 wt. % result in about four to six molecular layers being bonded to the surface. (For bulk depositions, higher reagent concentrations of up to approximately 50 wt. % may be necessary.) These about four to six intermediate layers are preferred as they ensure that there are no remaining unreacted silanol groups but yet permit a substantial electroosmotic flow. The other functional group of the silylating reagent is a nitrogen nucleophile, an oxygen nucleophile, or a carbon electrophile. Silylating reagents yielding oxygen nucleophiles are preferred and these include: 3-glycidoxypropyldimethylethoxysilane, (3-glycidoxypropyl)methyldiethoxysilane, 3-glycidoxypropylmethyl-diisopropenoxysilane, and (3-glycidoxypropyl)trimethoxysilane. Suitable exemplary silylating reagents yielding either a nitrogen nucleophile, an oxygen nucleophile, or a carbon electrophile are described in U.S. Pat. No. 5,006,313.

It has been found that by increasing the time of deposition and/or the concentration of the silylation reagent, the thickness of the intermediate layer can be increased so as to reduce the EOF to a desired level. In one series of experiments, the intermediate layer was built up by polymerization of a monomer concentration in the range of 0.1% to 50% in time intervals from 15 minutes to two hours. The EOF, which is dependent on the strength of the applied electric field, ranges from approximately 0.5 to 1.5 mm/sec when the electric field strength is from about 200 to 500 V/cm. Furthermore, after agarose was bonded to the intermediate layer, it was found that the cathodic EOF magnitude remained relatively constant even if the pH of the running buffer fluctuated from approximately 4-7.

EXPERIMENTAL

In a preferred method of preparing the inventive capillaries, silica capillary tubing (Polymicro Technologies) having 25-75 μ inner diameter was first hydrated with 0.1N KOH by pumping the solution through the capillary at a rate of about 1-2 μ/l minute for an 8-10 hour period. The capillary was then washed for 2-3 hours with DI water. The silylation solution used was a 1% glycidoxypropyltriethoxysilane (GOPS) in 80% ethanol which had been acidified to approximately pH 3-4. The silylation solution was allowed to pass through each end of the capillary at 1-2 column volumes per minutes for 0.5 hours. (For bulk deposition with GOPS, a 50% GOPS solution is used and the silylation solution is allowed to pass through the capillary for approximately 1 hour.) The coating was then cured by passing dry helium through the tubes overnight. Thereafter the diol surface was activated with the bifunctional reagent glutaraldehyde whereby a 20% aqueous solution of glutaraldehyde was flushed through the columns at a flow rate of 1-2 column volumes per minute for 10-15 minutes. The columns were then sealed using a TEFLON sleeve and incubated for 2 hours at 80° C. The capillary was unsealed and excess reagent was rinsed from the capillary with about 500 μl of 0.1 N phosphate buffer at ph 7. Thereafter, a 0.25% agarose solution (IEF grade, FMC Corp.) was flushed through the capillary and then resealed. After incubating overnight at 80° C., the capillary was unsealed and excess agarose was flushed from the capillaries with buffer. The capillary was equilibrated with many column volumes (1 ml) of running buffer before use.

To test the effectiveness of the inventive capillaries with respect to reversible interactions with protein solutes, the EOF and efficiencies (N) of the capillaries were measured before and after protein injections in a CZE apparatus which comprised of either an HP 3D-CE TM (Hewlett-Packard, Palo Alto, Calif.) or a Spectraphoretic 500 (Spectra-Physics Analytical, Fremont, Calif.). Sample injections were automated.

Two basic proteins, cytochrome c and lysozyme, were chosen as the "worse case" examples. EOF determinations employed DMSO as the EOF marker which bracketed protein determinations. Table 1 tracks the column history for an inventive agarose modified column beginning with (I) a 25 μ inner diameter untreated (bare) silica capillary, followed by (2) the capillary after silylation with GOPS, and finally (3) the inventive capillary as modified with agarose. The running buffer was 20 mM phosphate, pH 7.0, 30° C. A three minute rinse (with running buffer) followed each determination. The efficiency and EOF were measured before and after the cytochrome c was injected into the capillary. As is apparent, with respect to the agarose modified capillary, the EOF did not change significantly after the cytochrome c was injected.

Table 2 tracks the column history for a second agarose modified capillary. The efficiency and EOF were measured before and after injections of: (1) cytochrome c; (2) lysoyme; (3) buffer; and (4) cytochrome c. A 3 minute buffer rinse followed each determination. As is apparent, the EOF did not change significantly due to the cytochrome c injections. But after injection with lysozyme, the 3 minute buffer wash did not restore the original response. However, an additional 30 minutes wash (Step 3) significantly restored both the efficiency and electroosmotic flow. Indeed, after the wash the efficiency was restored almost to the level prior to any protein injection. This demonstrates the effective removal of the protein solutes from the surface during the wash step thereby restoring column performance.

Table 3 tracks the column history for a commercial HPCE column that has a hydrophobic inner surface. The efficiency and EOF were measured (1) before cytochome c was injected, and (2) after cytochrome c injection following a three minute buffer rinse. As is apparent, the EOF changed significantly after each protein injection.

TABLE 1

| Condition of Column | N(preprotein) | N(postprotein) | EOF(preprotein) (mm/sec) | EOF(postprotein) (mm/sec) |
| --- | --- | --- | --- | --- |
| 1. bare silica | 48,762 | N/A | 0.43 | N/A |
| 2. GOPS | 78,632 | N/A | 1.36 | N/A |
| 3. Modified w/ agarose | 80,431 | 66,085 | 0.89 | 0.87 |

TABLE 2

| Injection | N(preprotein) | N(postprotein) | EOF(preprotein) (mm/sec) | EOF(postprotein) (mm/sec) |
| --- | --- | --- | --- | --- |
| 1. Cyto c[1] | 49,716 | 48,303 | 0.61 | 0.62 |
| 2. Lyso[1] | 48,303 | 33,772 | 0.62 | 0.31 |
| 3. 30 minute[1] column wash (buffer) | 33,772 (prebuffer) | 60,808 (postbuffer) | 0.31 | 0.66 |
| 4. Cyto c[2] | 31,570 | 45,488 | 0.33 | 0.32 |

[1] 20 mM phosphate, pH 7.0 + 8 mM CHAPSO 30° C.
[2] 50 mM OAc, pH 4.6 + 15 mM CHAPS 30° C.

TABLE 3
SUMMARY OF PERFORMANCE OF SUPELCO C18 COLUMNS

| Condition | N(preprotein) | N(postprotein) | EOF(preprotein) (mm/sec) | EOF(postprotein) (mm/sec) |
| --- | --- | --- | --- | --- |
| 1. 20 mM phosphate pH 7.0; 25° C. | 44,700 | 33,219 | 0.80 | 0.74 |
| 2. 20 mM phosphate pH 7.0; 25° C. + 6 mM CHAPS | 61,197 | 36,664 | 0.58 | 0.54 |

The comparator data of Tables 1, 2, and 3 demonstrate that agarose modified capillary surfaces provide reproducibility after protein injections which is required for HPCE.

Advantages of the invention were also demonstrated by CZE analyses of triplicate protein sample injections employing three different columns, namely: (1) an untreated (bare) silica capillary, (2) a capillary treated with GOPS, and (3) an agarose modified inventive capillary. In this experiment, a standard sample mixture, containing 18 protein species separated by a single charge and with pI ranging from 4.5 to 10.0, was injected into a CZE apparatus for analysis. Following a 3 minute buffer rinse, the injection, CZE analysis, and rinse were twice repeated in the same CZE device. Each of the three different columns were so tested.

FIGS. 1(a), 1(b), and 1(c) show three electropherograms representing the triplicate injections into a CZE device with a 75 μ inner diameter untreated silicon capillary. The running buffer comprised 25 mM Pi; NH4+ and 2M urea. As is apparent, resolution of the proteins was nil. Moreover, as shown in FIGS. 1(b) and 1(c), for the two electrophoretic separations where proteins broke through, the elution times were not reproducible. (Apparently, proteins in the first injection deactivated the capillary surface enough to allow proteins in subsequent injections to break through to a point detection.)

FIGS. 2(a), 2(b), and 2(c) show electropherograms for triplicate injections into a CZE device with a 75 μ silica capillary that was silylated with GOPS. Although resolution in the GOPS modified columns is better than the resolution in the untreated silica columns, the electropherograms also show that resolution decreased with each successive injection. Most likely the deterioration of the separation was caused by protein solutes irreversibly adhering to the inner bore. Furthermore, the electropherograms of FIGS. 2(b) and 2(c) show a shift in the elution time relative to the initial electropherogram of FIG. 2(a).

FIGS. 3(a), 3(b), and 3(c) show electropherograms for triplicate injections into a CZE device with a 75 μ agarose modified capillary (pretreated with GOPS). Although not all 18 proteins were resolved, the electropherograms demonstrate the improvement in separation reproducibility vis-á-vis both the untreated silica capillary and the silylated capillary. In addition, with the inventive capillary, the separation efficiency and elution times remained relatively constant after the first injection. This connotes the effective removal of protein solutes which may have adhered to the column during the analysis.

FIGS. 4(a) and 4(b) are electropherograms of the above referenced mixture of 18 proteins in a CZE device with a 75 μ inner capillary that was treated either with bovine serum albumin (BSA) (FIG. 4(a)) or with agarose (FIG. 4(b)). The inner surfaces of both capillaries were pretreated with GOPS. (The BSA proteins provide an amphoteric phase along the inner surface. See U.S. Pat. No. 4,931,328.) The running buffer (pH 5.0) comprised 50 mM OAc and 18 mM nonyl glucoside. A comparison of FIGS. 4(a) and FIG. 4(b) shows another aspect of the present invention which is that the agarose modification versus the BSA modification displays distinct surface selectivity in protein separations. The electropherogram of FIG. 4(a) shows that 10 of the proteins in the mixture were resolved in the BSA modified column. In contrast, only 8 of the proteins were resolved in the agarose modified column as shown in the electropherogram of FIG. 4(b). It is believed that the ten proteins resolved in the BSA modified column do not include all eight proteins resolved in the agarose modified column. Thus, with the inventive agarose modified column, it is be possible to resolve proteins that are not otherwise resolved in some conventional columns.

Surface selectivities for a particular column can be calculated with respect to specific protein solutes by comparing the relative mobilities of the solutes. For instance, comparison of the selectivities (i.e. mobility ratios) of different protein solute pairs separated in different columns but under the same CZE conditions provides information regarding each column's selectivity for the various proteins. See Maa, *J. High Resol. Chromatog.*, 14 (1991), pp. 66-67.

FIG. 5 illustrates the main components of a CZE apparatus. An injection end of a separation capillary 10 extends into an inlet reservoir 12 that holds the analyte 14 and, using any known method, injects it into or allows it to enter the capillary. A known power source 16 applies an electric field over the length of the capillary 10. After entering the injection end of the capillary 10, the analyte passes through the capillary, past a conventional detector 18, and empties into an outlet reservoir 20. According to the invention, the capillary 10 is provided with the agarose coating described above.

It is to be understood that while the invention has been described above in conjunction with preferred specific embodiments, the description and examples are intended to illustrate and not limit the scope of the invention, which is defined by the scope of the appended claims.

What is claimed is:

1. A device for electrophoretic separations of protein solutes, comprising:
   a capillary tube that has an inner wall;
   reservoir and injection means for holding analyte that includes the protein solutes and for injecting the analyte into the capillary tube;
   power supply means for applying an electric field along the capillary tube;
   detection means for detecting separated solutes within the capillary tube; and
   means for providing reversible interactions between the protein solutes and the inner wall and including an interfacial layer, which includes agarose and is bonded coavalently to the inner wall.

2. A device for electrophoretic separations of protein solutes, comprising:
   a capillary tube that has an inner wall;
   an interfacial layer bonded to the inner wall;
   reservoir and injection means for holding analyte that includes the protein solutes and for injecting the analyte into the capillary tube;
   power supply means for applying an electric field along the capillary tube;
   detection means for detecting separated solutes within the capillary tube; and
   an outer layer including agarose that is covalently bonded to the interfacial layer;
   whereby interactions between the protein solutes and the inner wall are reversible.

3. A device as defined in claim 2, in which the interfacial layer is a reaction product of a silylating reagent and silanol groups.

4. A device as defined in claim 3, in which the interfacial layer has a deposition thickness corresponding to a monomer concentration in the range of 0.1% to 50% that has polymerized for a time period in the range of 15 minutes to two hours, whereby the interfacial layer provides a predetermined electroosmotic flow within the capillary having a magnitude that remains substantially constant for a buffer having a pH that ranges from 4 to 7.

5. A method for treating a solid silica inner wall surface of an electrophoresis capillary exposable to protein solutes comprising the steps of:
   depositing an interfacial layer on the inner wall surface; and
   depositing, by covalently bonding, an outer layer containing agarose on the interfacial layer;
   whereby interactions between the protein solutes and the inner wall are reversible.

6. A method as defined in claim 5, in which the interfacial layer is a bifunctional silylating reagent including a functional group consisting of an alkoxy or chloro group.

7. A method as defined in claim 6, including the step of depositing the interfacial layer as a monomer in a concentration in the range of 0.1% to 50% for a polymerization period in the range of 15 minutes to two hours, whereby the interfacial layer provides a predetermined electroosmotic flow within the capillary having a magnitude that remains substantially constant and corresponds to a deposition thickness of the interfacial layer.

8. A method as defined in claim 7, in which intermediate layer is a reaction product of the silylating reagent and silanol groups on the solid silica surface.

9. A coated capillary in a capillary electrophoresis apparatus for electrophoretic separations of protein solutes, comprising:
   a capillary tube that has an inner wall;
   an interfacial layer bonded to the inner wall; and
   an outer layer including agarose that is coavalently bonded to the interfacial layer;
   whereby interactions between the protein solutes and the inner wall are reversible.

10. A capillary as defined in claim 9, in which the interfacial layer is a reaction product of a silylating reagent and silanol groups.

11. A capillary as defined in claim 10, in which the interfacial layer has a deposition thickness corresponding to a monomer concentration in the range of 0.1% to 50% that has polymerized for a time period in the range of 15 minutes to two hours,
   whereby the interfacial layer provides a predetermined electroosmotic flow within the capillary having a magnitude that remains substantially constant for a buffer having a pH that ranges from 4 to 7.

* * * * *

UNITED STATES PATENT AND TRADEMARK OFFICE
CERTIFICATE OF CORRECTION

PATENT NO. : 5,314,593
DATED : May 24, 1994
INVENTOR(S) : Sally A. Swedberg

It is certified that error appears in the above-indentified patent and that said Letters Patent is hereby corrected as shown below:

Column 1, line 53, "*Chem.*" should read -- *Chrom.* --;

Column 1, line 54, "*Biol.*, (1992)" should read -- *Biol.*, 37 (1992) --;

Column 5, line 39, "$\mu/1$ minute" should read -- $\mu$l/minute--;

Column 6, line 23, "(I)" should read -- (1)--;

Column 6, line 37, "lysoyme" should read -- lysozyme--;

Column 7, line 24, "comparator" should read -- comparative --;

Column 8, line 25, "vis-á-vis" should read -- vis-à-vis --.

Signed and Sealed this

Eleventh Day of October, 1994

Attest:

BRUCE LEHMAN

*Attesting Officer*    *Commissioner of Patents and Trademarks*